US00PP37126P2

(12) United States Plant Patent
Clarkson et al.

(10) Patent No.: US PP37,126 P2
(45) Date of Patent: Dec. 9, 2025

(54) ***RUBUS* PLANT NAMED 'BWPRASP03'**

(50) Latin Name: ***Rubus* hybrid**
Varietal Denomination: BWPRASP03

(71) Applicant: BerryWorld Plus Limited., Henley-On-Thames (GB)

(72) Inventors: Graham John Joseph Clarkson, Faversham (GB); Dulce Coelho, São Brás de Alportel (PT)

(73) Assignee: BERRYWORLD PLUS LIMITED., Henley-on-Thames (GB)

( * ) Notice: Subject to any disclaimer, the term of this patent is extended or adjusted under 35 U.S.C. 154(b) by 0 days.

(21) Appl. No.: 19/039,956

(22) Filed: Jan. 29, 2025

(30) Foreign Application Priority Data

Jul. 8, 2024 (QZ) ..... PBR 20241607

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/0887
See application file for complete search history.

*Primary Examiner* — Kent L Bell
(74) *Attorney, Agent, or Firm* — Penny J. Aguirre

(57) ABSTRACT

A new cultivar of *Rubus* hybrid plant named 'BWPRASP03' that is characterized by its fruit production on primocanes, by its high primocane fruit yields, its early cropping profile, its medium red fruits that are consistently large in size throughout the season, its very good extended shelf life, by its fruit that is easy to pick with low adherence to the plug, its primocanes that are upright, moderately branched and have large leaflets, and its sweet fruit with relatively low acidity.

4 Drawing Sheets

Botanical classification: *Rubus* hybrid.
Cultivar designation: 'BWPRASP03'.

CROSS-REFERENCE TO RELATED APPLICATIONS

This application claims priority to European Community Plant Variety Office (CPVO) Plant Breeder's Rights Application No. 2024/1607 filed on Jul. 8, 2024, under 35 U.S.C. 119(f), the entire contents of both applications which are incorporated by reference herein. This application is also related to United Kingdom Plant Variety Office (UPOV) Application No. 18/121 filed on Oct. 16, 2024. The information for the plant breeders' rights applications was received directly from the Inventors.

BACKGROUND OF THE INVENTION

The present invention relates to a new and distinct cultivar of raspberry plant, botanically thought to be of hybrid origin with *Rubus idaeus* and other species in its ancestry. 'BWPRASP03' will be referred to hereinafter by its cultivar name, 'BWPRASP03'. 'BWPRASP03' is a new red raspberry plant grown for the fresh fruit market.

'BWPRASP03' arose from an on-going breeding program conducted by the Inventors. 'BWPRASP03' arose from a cross made in Spring 2019 in Faversham, Kent, United Kingdom between an unnamed and an unpatented proprietary plant in the Inventors' breeding program; designated as accession code "JAH-V2" as the female parent, and patented variety 'PWPRASP01' (U.S. Plant Pat. No. 32,721) as the male parent. The new cultivar was selected in the winter of 2020 to 2021 in Cartaya, Huelva, Spain as accession code "PCR-W2" from the seedlings that resulted from the above cross.

Asexual propagation of the new cultivar was first accomplished by one of the Inventors by root cuttings in Cartaya, Huelva, Spain in spring of 2021. Asexual propagation of the new cultivar by root cuttings and terminal stem cuttings has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'BWPRASP03' as a new and unique cultivar of *Rubus*.

1. 'BWPRASP03' exhibits fruit production on primocanes.
2. 'BWPRASP03' exhibits high primocane fruit yields.
3. 'BWPRASP03' exhibits an early cropping profile.
4. 'BWPRASP03' exhibits medium red fruits that are consistently large in size throughout the harvest season.
5. 'BWPRASP03' exhibits a very good extended shelf life.
6. 'BWPRASP03' exhibits fruit that is easy to pick with low adherence to the plug.
7. 'BWPRASP03' exhibits primocanes that are upright, moderately branched and have large leaflets.
8. 'BWPRASP03' exhibits sweet fruit with relatively low acidity.

The female parent of 'BWPRASP03' differs from 'BWPRASP03' in having fruit that is yellow in color with less coherent drupelets, less firm drupelet skin, less shelf life, less sweet tasting fruit and more difficult to pick. The male parent of 'BWPRASP03' differs from 'BWPRASP03' in having fruit that is lighter red in color with larger drupelets, more thorns that are larger, smaller leaves that are less glossy, and a later cropping profile with a much lower primocane fruit yield. 'BWPRASP03' can be compared to *Rubus* cultivars 'Diamond Jubilee' (U.S. Plant Pat. No. 25,455) and 'Autumn Glory' (U.S. Plant Pat. No. 25,952). 'Diamond Jubilee' differs from 'BWPRASP03' in having lower fruit yields, a later cropping profile, smaller fruit throughout the season, indents on the druplets ('BWPRASP03' druplets are smooth), canes with more anthocyanin coloration with larger leaflets, and less density of thorns on the peduncle and pedicel. 'Autumn Glory' differs from 'BWPRASP03' in producing fruit that is much smaller in size with a later cropping profile, is darker in color, much harder to pick, and exhibits a reduced shelf life.

BRIEF DESCRIPTION OF THE DRAWINGS

The accompanying color photographs illustrate the overall appearance and distinct characteristics of the new *Rubus*. The photographs were taken of plants 18 months in age as grown in a high poly tunnel in 7-liter square containers in Faversham, United Kingdom.

The photograph in FIG. 1 provides a view of the fruiting canes of 'BWPRASP03 '.

Figure 1:
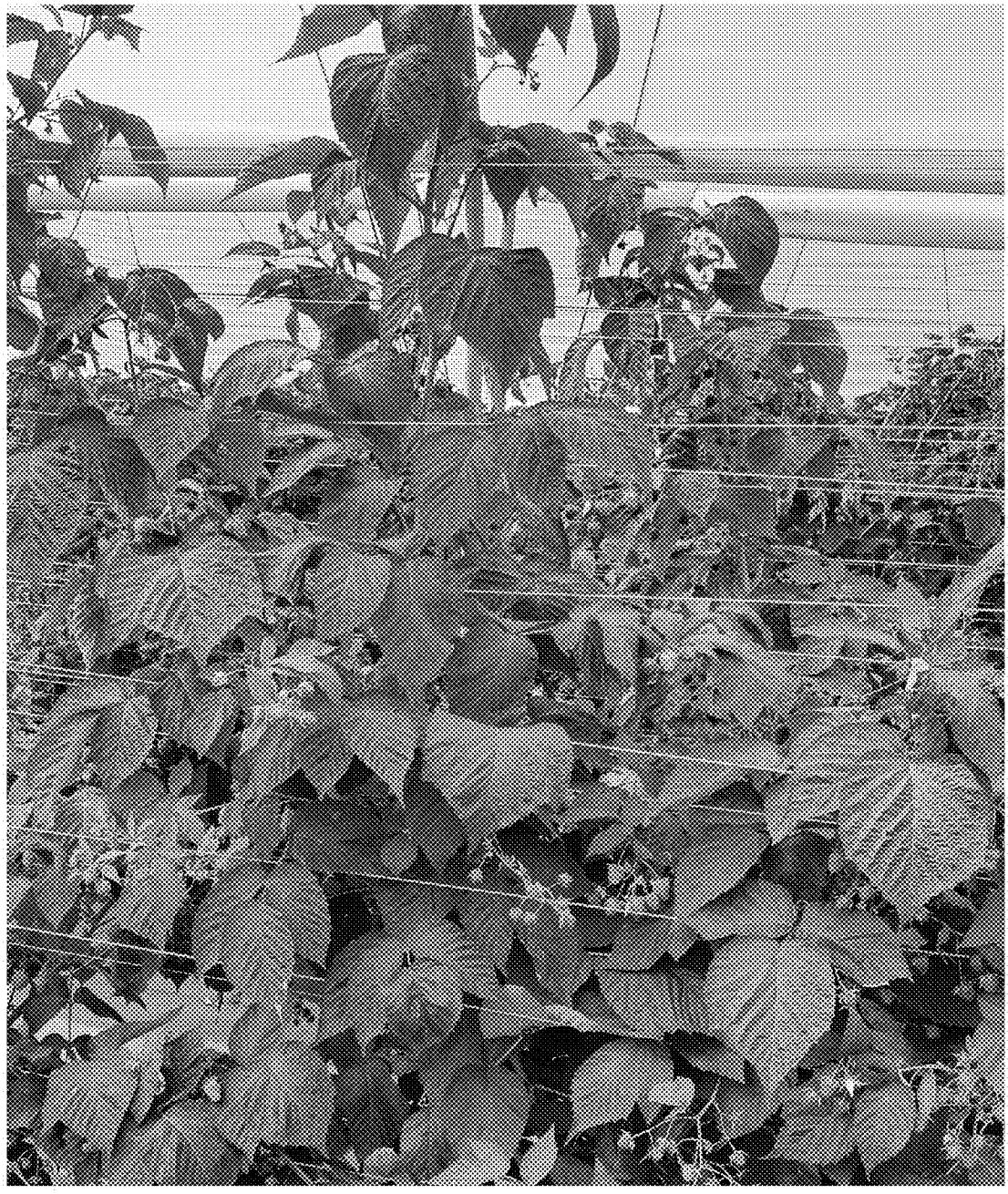
Figure 2:
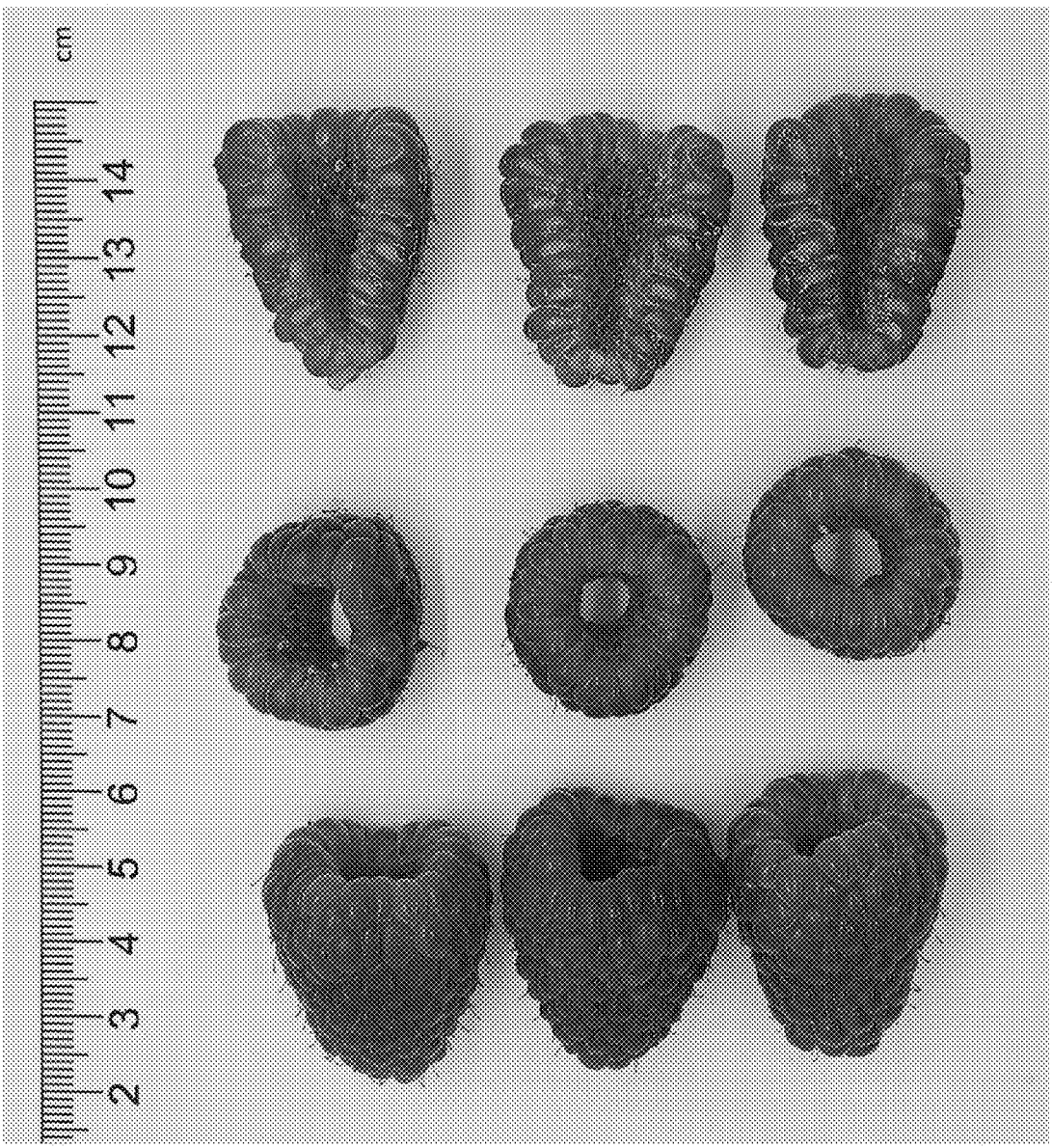

The photograph in FIG. 2 provides a close-up view of the fruit of 'BWPRASP03'; longitudinally cut fruit (top), top view of whole fruit (middle), side view of whole fruit (bottom).

Figure 3:
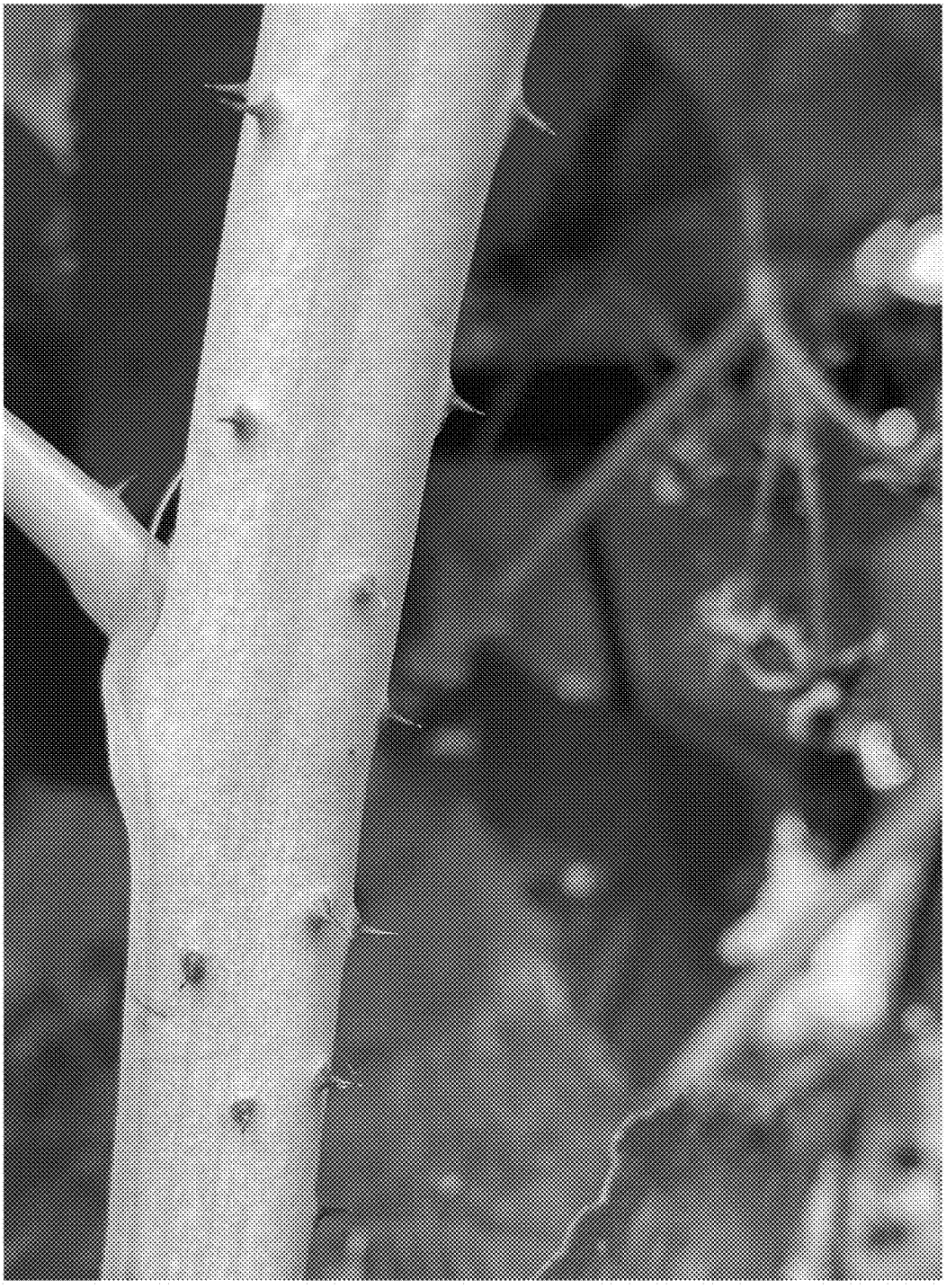

The photograph in FIG. 3 provides a close-up view of the primocane spines of 'BWPRASP03'.

Figure 4:
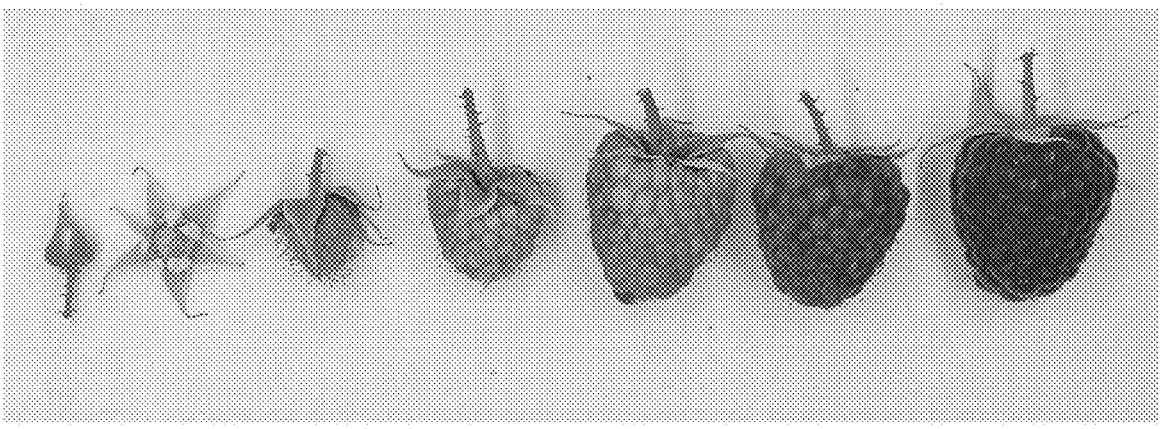

The photograph in FIG. 4 provides a view of the developing flower buds and developing fruits of 'BWPRASP03'.

The colors in the photographs are as close as possible with the photographic and printing technology utilized and the colors may differ slightly from the color values cited in the detailed botanical description, which accurately describe the colors of the new *Rubus*.

DETAILED BOTANICAL DESCRIPTION OF THE PLANT

The following is a detailed description of plants about 18 months in age as grown in a high poly tunnel in 7-liter square containers in Faversham, United Kingdom. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England (6th Edition), except where general color terms of ordinary dictionary significance are used.

General description:

*Blooming period.*—Primocane; Mid to late June in Faversham, Kent, The United Kingdom.

*Plant type.*—Fruit bearing perennial, fruit borne on primocanes.

*Plant habit and shape.*—Upright with long laterals, roughly columnar in shape.

*Height and spread.*—Between 1.2 and 1.7 m in height and 0.7 to 1.4 m in width (measured at tip of plant at time of fruit production).

*Hardiness.*—At least in U.S.D.A Zones 8 to 10.

*Diseases and pests.*—This variety has not shown any specific susceptibility or resistance to pests or diseases.

*Root description.*—Fibrous and vigorous.

*Propagation.*—Root cuttings and terminal stem cuttings.

*Root development.*—Root cuttings fully root in 2 weeks in a coir plug and fully develop in a 4.7-liter container in about 4 months.

*Growth rate.*—Vigorous.

Cane description (primocanes):

*Cane size.*—Between 1.2 m and 1.7 m in length and on average 1.5 mm in diameter (20 cm from base).

*Cane color.*—144D, weak anthocyanin 63A in color.

*Internode length.*—Average 7.4 cm measured at middle of cane.

*Branching habit.*—Moderately branched.

*No of current season shoots.*—35 to 60 during fruiting season.

*Fruiting laterals.*—An average of 22 fruiting laterals per cane, verage of 16.8 cm in length at 35 cm from tip and 39.5 cm in length at 70 cm from tip, 144C in color with anthocyanin coloration 63A, surface glabrous.

*Spines.*—Spines sparse on canes, medium density on peduncle with an average of 5.8 per 5 cm segment, spines are tapered with wide base and thin point and the apex is either straight at 90° angle or slightly angled at 45° attitude in relation to cane, spines are on average 1.9 mm in length, 2.6 mm in width, 60A in color, brittle and tips break easily, non-glaucous.

Foliage description:

*Leaf shape.*—Compound shape, odd pinnate orientation.

*Leaf division.*—Compound; equally three and five leaflets.

*Leaf attachment.*—Petiolate.

*Leaf orientation.*—Flat to pendant.

*Leaf size.*—An average of 29 cm in length and 27.8 cm in width; 1:1 ratio.

*Leaflet shape.*—Cordate on terminal, ovate on basal leaflets.

*Leaflet base.*—Cordate on terminal, rounded on basal leaflets.

*Leaflet apex.*—Acuminate.

*Leaflet venation.*—Pinnate, color primarily matches leaf color.

*Leaflet margins.*—Biserrate to erose, un-lobed, low to moderate undulation.

*Relative position of lateral leaflet.*—Opposite and free to touching leaflets.

*Profile of leaflet cross section.*—V-shaped concave, curves upwards away from main vein.

*Leaflet arrangement.*—One terminal and 1 to 2 lateral pairs.

*Leaflet attachment.*—Petiolate.

*Leaflet surface.*—Glabrous on both surfaces with moderate rugosity between veins on upper surface.

*Leaflet color.*—Upper surface moderate 137A, lower surface 148B.

*Leaflet size.*—Terminal; an average of 15.8 cm in length and 10.8 cm in width (ratio 1:5), basal; an average of 15.8 cm in length and 10.7 cm in width (ratio 1:5).

*Petioles*.—Round in shape, an average of 8.3 cm in length and 3.3 mm in width, color upper surface 144A, color lower surface 145A, texture is smooth to touch with extremely fine pubescence and very sparse spines.

*Stipules*.—2 per petiole, erect at nodes, grows parallel to new growth, light pubescence but mainly smooth, an average of 1.11 cm in length and 0.9 mm in width, lanceolate in shape, color 144B.

*Rachis*.—Round in shape, an average of 6.5 cm in length and 2.6 mm in width, 145A in color, surface has spines on lower surface.

Inflorescence description:

*Inflorescence*.—Raceme.

*Pedicels*.—Oval in shape, an average of 4.58 cm in length and 1.4 mm in width, color 144A, surface glabrous with thorns, strong (doesn't break easily when bent or detach easily from plant).

*Flower type*.—Spreading calyx with a center ring of numerous upright stamens and with numerous pistils in the center, moderate petal retention when flowers open, petals are shed early in fruit maturation.

*Flower fragrance*.—Faint, fruity-floral.

*Flower size*.—3.37 cm in diameter.

*Flower number per lateral*.—An average of 53.

*Sepals*.—Between 5 and 6, base truncate, apex acuminate, margins entire, triangular in shape, both surfaces: center color 144A, outer color 144D, anthocyanin absent, both surfaces have slight pubescence with vary faint veins.

*Peduncle*.—On average 38 cm in length and 2 mm width, N144A in color, strong, surface smooth with thorn density medium.

*Petals*.—Between 5 and 6 per flower, individually attached, dropped at fruit maturity, an average of 8 mm in length and 3.8 mm in width, spatula in shape with a rounded apex and oblong base, entire margins, both surfaces: color NN155A, surface texture glabrous.

*Fertility*.—Self-compatible.

*Pistils*.—An average of 120, 157A in color.

*Stamens*.—An average of 121, NN155A in color, pollen is moderate in quantity and 159C in color.

Fruit description:

*Fruit size*.—Average of 2.94 cm in length and 2.5 cm in width, ratio 1:2.

*Fruit color*.—Immature; 152D, early maturing; 168A, maturing; 42B, ripe; 44A.

*Fruit shape*.—The aggregate fruit is broad conical.

*Fruit adherence to plug*.—Medium but easy to pick.

*Drupelets*.—An average of 149.8 drupelets per aggregate fruit, globose in shape and firm, 5 to 7 mm in length and width, surface is moderately glossy, style and stigma; persistent at maturity, smooth, usually uncreased and undented.

*Receptacle*.—Conical and pointy in shape, persistent on the plant at harvest, fleshy, size varies with individual fruit size.

*Fruit maturity date*.—Early ripening, mid-July in Kent, United Kingdom.

*Seed*.—Kidney shaped, 1 per drupelet, an average of 3.5 mm in length and 1.5 mm in width, 161B in color.

*Cropping frequency*.—Produced on same year cane (primocanes), versatile cropping schedule as it can be established on different planting dates throughout spring to maintain a fruiting season from summer to late autumn in Faversham, Kent, United Kingdom.

*Flavor*.—Sweet.

*Brix*.—10.4° under conditions grown.

*Acidity*.—0.99 TTA.

*Brix:acid ratio*.—10.5:1.

*Yield*.—Average of 4,350 Class I g/pot from mid-July to mid-September.

*Fruit weight*.—Average 7.9 g.

*Market use*.—Fresh fruit, commercial production.

*Shelf life*.—Extended, fruits can be transported and kept in chilled conditions without noticeable deterioration for 7 or more days after harvest.

It is claimed:

1. A new and distinct cultivar of *Rubus* hybrid plant named 'BWPRASP03' as hercin illustrated and described.

* * * * *